US007250520B2

(12) United States Patent
Wallace

(10) Patent No.: US 7,250,520 B2
(45) Date of Patent: Jul. 31, 2007

(54) PROCESSES FOR PREPARING PYRROLES

(75) Inventor: Michael Wallace, West Chester, PA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 10/978,301

(22) Filed: Oct. 28, 2004

(65) Prior Publication Data

US 2005/0143585 A1 Jun. 30, 2005

(51) Int. Cl.
*C07D 207/32* (2006.01)

(52) U.S. Cl. .................................................... 548/533

(58) Field of Classification Search ................. 548/533
See application file for complete search history.

(56) References Cited

U.S. PATENT DOCUMENTS

2004/0018986 A1* 1/2004 Pitlik et al. ................... 514/19
2005/0080017 A1* 4/2005 Cottrell et al. ................ 514/19

OTHER PUBLICATIONS

Ueda, et al. "A Novel One-Pot Synthesis of Pyrroles From 1, 2, 5-Selenadiazole and 1,3-Diketones" J. Chem. Soc. Perkin Trans. 1, (1994), pp. 2201-2202.*

Falk et al. "Selectivity Problem in the Synthesis of Pyrrole" Monatsh. Chem. (1973), 104(4), pp. 925-932.*

Fischer et al. "A New Pyrrole Synthesis" Z. Physiol. Chem. (1944), 280, pp. 123-126.*

Fischer et al., "A New Synthesis of Pyrroles" Z. Phisiol. Chem. (1948) 282, pp. 152-161.*

Cesarino Balsamini et al. "(E)-3-(2-(N-Phenylcarbamoyl)vinyl)pyrrole-2-carboxylic Acid Derivatives. A Novel Class of Glycine Site Antagonists" Journal of Medicinal Chemistry, vol. 41, No. 6, 1998, pp. 808-820.

Matthias Lehr et al. "Synthesis, Biological Evaluation, and Structure-Activity Relationships of 3-Acylindole-2-carboxylic Acids as Inhibitors of the Cytosolic Phospholipase $A_2$" Journal of Medicinal Chemistry. 1997, vol. 40, No. 17, 1997, pp. 2694-2705.

* cited by examiner

*Primary Examiner*—Kamal A. Saeed
*Assistant Examiner*—Nyeemah Grazier
(74) *Attorney, Agent, or Firm*—Susan C. Kelly; Lisa A. Dixon

(57) ABSTRACT

The present invention relates to an improved synthesis of pyrrole capping group precursors.

25 Claims, No Drawings

PROCESSES FOR PREPARING PYRROLES

TECHNICAL FIELD OF THE INVENTION

The present invention relates to processes for preparing compounds useful in the synthesis of biologically active compounds, particularly protease inhibitors.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," *J. Hepatology,* 31., (Suppl. 1), pp. 17–24 (1999)]. Nearly four million individuals may be infected in the United States alone [M. J. Alter et al., "The Epidemiology of Viral Hepatitis in the United States, *Gastroenterol. Clin. North Am.,* 23, pp. 437–455 (1994); M. J. Alter "Hepatitis C Virus Infection in the United States," *J. Hepatology,* 31., (Suppl. 1), pp. 88–91 (1999)]. Unfortunately, there are no broadly effective treatments for the debilitating progression of chronic HCV.

There are not currently any satisfactory anti-HCV agents or treatments. Until recently, the only established therapy for HCV disease was interferon treatment. However, interferons have significant side effects [M. A. Wlaker et al., "Hepatitis C Virus: An Overview of Current Approaches and Progress," *DDT,* 4, pp. 518–29 (1999); D. Moradpour et al., "Current and Evolving Therapies for Hepatitis C," *Eur. J. Gastroenterol. Hepatol.,* 11, pp. 1199–1202 (1999); H. L. A. Janssen et al. "Suicide Associated with Alfa-Interferon Therapy for Chronic Viral Hepatitis," *J. Hepatol.,* 21, pp. 241–243 (1994); P. F. Renault et al., "Side Effects of Alpha Interferon," *Seminars in Liver Disease,* 9, pp. 273–277. (1989)] and induce long term remission in only a fraction (~25%) of cases [O. Weiland, "Interferon Therapy in Chronic Hepatitis C Virus Infection", *FEMS Microbiol. Rev.,* 14, pp. 279–288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

The HCV nonstructural (NS) proteins are presumed to provide the essential catalytic machinery for viral replication. The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery.

Protease inhibitors and many other compounds comprise N-terminal capping groups. Such N-terminal capping, or protecting, groups are not limited to HCV protease inhibitors. Any peptidyl biologically active compound may have an N-terminal capping group. Similarly, many non-peptidyl (particularly peptidyl mimetic) compounds comprise the equivalent of an N-terminal capping group. Furthermore, a primary or secondary amine in any compound could be derivatized with a capping group. Accordingly, N-terminal capping groups are widely used. There is therefore a need for N-terminal capping groups (sometimes referred to as protecting or protective groups) and methods for making such groups.

A pyrrole-based capping group that is particularly useful has been described (WO 03/087092). This capping group is relatively complex. A disadvantage of relatively complex capping groups is that they may not be readily available commercially and/or may be difficult to synthesize. As is known, carboxylic acids are convenient precursors for such capping groups. Unfortunately, there are no safe, efficient, and/or large-scale methods for synthesizing the carboxylic acid precursors corresponding to these particularly useful capping groups (see, D. T. Kozhich et al., *Zh. Organ. Khimii,* 16 pp. 849–855–750 (1980); UDC 547, 745: 312; A. J. Robinson et al., *J. Org. Chem.* 66, pp. 4148–4152 (2001); H. Falk et al. *Monatsh. Chemie,* 104, pp. 925–923 (1973)).

Thus, there is a need for efficient synthetic routes to these carboxylic acid precursors of pyrrole-based capping groups.

SUMMARY OF THE INVENTION

The present invention relates to an improved synthesis of a pyrrole capping group.

DETAILED DESCRIPTION OF THE INVENTION

This invention provides an improved synthesis of a carboxylic acid substituted pyrrole. Advantageously, this synthesis is amenable to large scale synthesis. Applicants' invention allows for the capping group to be more readily available.

Accordingly to a one embodiment (A), this invention provides a process for preparing a compound:

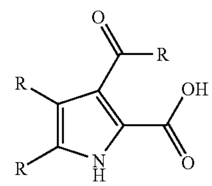

I-B, wherein:

each R is independently selected from an alkyl group; comprising;

a) reacting a compound of formula II-B:

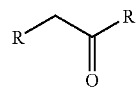

II-B, wherein each R is independently selected from an alkyl group, with a compound of formula III-B,

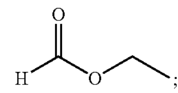

in the presence of NaOt-Bu (sodium t-butoxide), an appropriate solvent (such as THF) at an appropriate temperature to provide a compound of formula IV-B:

IV-B

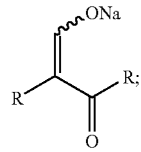

An appropriate reaction temperature in any embodiment of the above reaction is about 20° C. or less. In one embodiment a solution of butanone and an appropriate solvent (such as THF) is cooled to about −5° C. to about 15° C. (preferably about 0° C. to about 10° C.; alternatively about 5° C. to about 10° C.). In one embodiment the reaction is stirred overnight at about 20° C. to about 28° C. (preferably about 22° C. to about 26° C.).

Accordingly to another embodiment, this invention provides a process for preparing a compound:

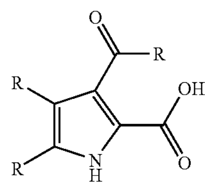

I-B; wherein each R is independently an alkyl group, comprising:

reacting a compound of formula IV-B:

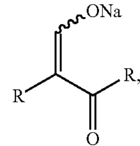

wherein each R is independently an alkyl group, and a compound of formula VI-B:

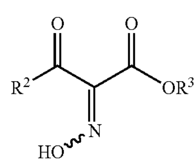

VI-B, wherein $R^2$ and $R^3$ are each independently an alkyl group; in the presence of zinc, acetic acid, water, and dioxane (or another appropriate solvent); to provide a compound of formula VI-B:

VI-B

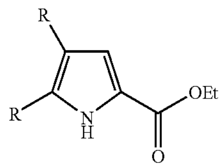

In a specific embodiment, $R^2$ is methyl.

In another specific embodiment, $R^3$ is methyl.

In one embodiment, the compound of formula IV-B, the compound of formula VI-B, water, dioxane (or other appropriate solvent), and acetic acid are reacted at about 50° C. to about 65° C. In a more specific embodiment the reaction mixture is stirred at about 58° C. to about 60° C.

In one embodiment, zinc is added (preferably portionwise) subsequent to the above heating step. This reaction mixture is then stirred at about 75° C. to about 85° C. In a more specific embodiment, the mixture is stirred at about 80° C. to about 85° C., more specifically at about 80° C. to about 82° C.

In one embodiment, the reaction mixture is extracted with t-butyl methyl ether (at about 25° C. to about 28° C.).

Advantageously, in this embodiment, no base (such as sodium acetate) is added.

In the embodiments of this invention, R is preferably a C-1 to C-6 alkyl group (including any integers therein). In a more specific embodiment each R is independently, a C-1, C2-, or C-3 alkyl group.

Accordingly to another embodiment (B), this invention provides a process for preparing a compound of formula I-a:

I-a

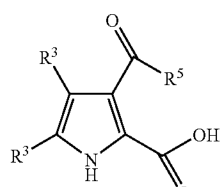

comprising:

combining an aqueous solution of the compound of formula IV-a:

IV-a wherein $R^3$ is $C_{1-12}$ aliphatic, $C_{3-12}$ alkyl-cycloaliphatic, $C_{3-12}$ alkyl-aryl, $C_{3-12}$ alkyl-heteroaryl, or $C_{3-12}$ alkyl-cycloaliphatic;

with a compound of formula V-a

V-a

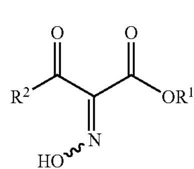

wherein $R^1$ and $R^2$ are each independently $C_{1-6}$ aliphatic; in the presence of zinc, water, and optionally an additional suitable solvent to form a compound of formula VI

VI

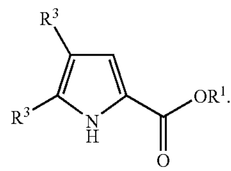

Applicants have found that using the compound of formula IV in an aqueous solution is advantageous. It should be understood that in aqueous conditions, the sodium hydrolyzes (i.e., dissociates to form an aldehyde. The sodium salt is easier to handle and more stable to store. However, it may be cumbersome to use in preparative methods. Applicant's method for pre-forming an aqueous solution of the salt is an improvement to the standard processes.

Another embodiment of this invention provides a process for preparing a compound of formula VI-a:

VI-a

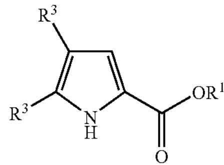

comprising, combining an aqueous solution of compound of formula IV-a:

IV-a

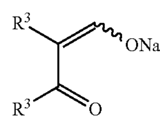

wherein $R^3$ is $C_{1-12}$ aliphatic, $C_{3-12}$ alkyl-cycloaliphatic, $C_{3-12}$ alkyl-aryl, $C_{3-12}$ alkyl-heteroaryl, or $C_{3-12}$ alkyl-cycloaliphatic;

with a compound of formula V-a

V-a

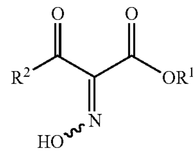

wherein $R^1$ and $R^2$ are each independently $C_{1-6}$ aliphatic in the presence of zinc and a suitable solvent to form the compound of formula VI.

Yet another embodiment provides a process for preparing a compound of formula I-a:

I-a

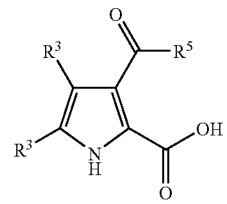

comprising,

A) combining an aqueous solution of the compound of formula IV-a:

IV-a

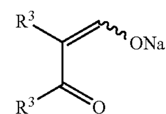

wherein $R^3$ is $C_{1-12}$ aliphatic, $C_{3-12}$ alkyl-cycloaliphatic, $C_{3-12}$ alkyl-aryl, $C_{3-12}$ alkyl-heteroaryl, or $C_{3-12}$ alkyl-cycloaliphatic;

with a compound of formula V-a

V-a

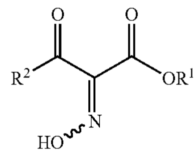

wherein $R^1$ and $R^2$ are each independently $C_{1-6}$ aliphatic; in the presence of zinc and a solvent comprising of water and optionally another suitable solvent (preferably a polar organic solvent, more preferably dioxane, THF, or other polar solvents) to form the compound of formula VI:

VI

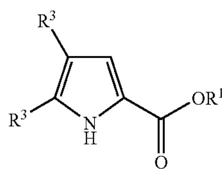

B) Acylating the compound of formula VI with a suitable acylating agent to form the compound of formula VII:

IX

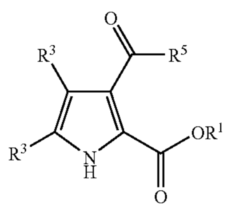

C) Hydrolyzing the compound of formula VII under suitable hydrolysis conditions (including acid or base hydrolysis, for metal hydroxides (see below for examples of metals, $H_2SO_4$(aq), HCl(aq)) to form the compound of formula I:

I

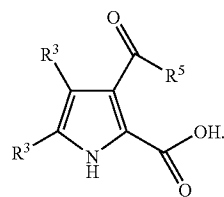

In certain embodiments of this invention (particularly in $R^3$) in alkylaryl and alkylheteroaryl groups, the aryl and heteroaryl is not alpha or beta relative to the position the alkyl is bound to the rest of the molecule. Preferably, the aryl and heteroaryl is at least at the gamma position or even farther from the bond. Aliphatic groups are preferably alkyl. Preferred forms of a $C_{1-12}$ group, is a $C_{1-6}$ group. The term "alkyl" and "aliphatic" as used herein means a straight chained or branched alkyl group.

In certain embodiments, the process further comprises reacting the compound of formula VI under suitable acylation conditions to provide a compound of formula IX

IX

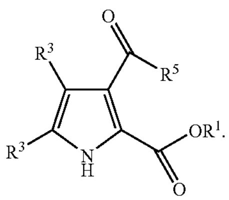

In certain embodiments, the compound of formula VI is reacted with $R^5$—X or $R^5C(=O)—O—C(=O)R^5$ to form the compound of formula IX wherein:

X is a suitable leaving group;

$R^5$ is $C_{1-12}$ aliphatic, aryl, heteroaryl, $C_{1-12}$ aliphatic-cycloaliphatic, $C_{1-12}$ aliphatic-aryl, $C_{1-12}$ aliphatic-heteroaryl, or $C_{1-12}$ aliphatic-cycloaliphatic. It should be understood that the reaction conditions tolerate a wide variety of $R^5$ groups.

In certain embodiments, the acylation conditions comprise:

heating the compound with $AlCl_3$ and $R^5C(=O)—O—C(=O)R^5$ to form the compound of formula IX.

In certain embodiments, the acylation conditions comprise:

heating the compound with $AlCl_3$ and $Ac_2O$ in refluxing dichloromethane to form the compound of formula IX wherein $R^5$ is methyl.

In certain embodiments, the process further comprises reacting the compound of formula IX under suitable hydrolysis conditions to provide a compound of formula I.

In certain embodiments, the hydrolysis conditions comprise:

a suitable base, a suitable solvent, and a reaction temperature between 20–100° C.

In certain embodiments, the process base is $M(OH)_n$, wherein M is a metal selected from lithium, sodium, potassium, cesium, magnesium, and calcium and n is 1–2, and/or the solvent is an alcoholic solvent. Preferred bases include KOH, the solvent is EtOH, and the temperature is that of refluxing ethanol.

In certain embodiments, the compound of formula IV, the compound of formula V, and a suitable acid are reacted in water and a suitable volume of an organic solvent to keep the reaction mixture in solution. The organic solvert is preferably selected to keep the reaction in solution.

In certain embodiments, the compound of formula IV, the compound of formula V, and acetic acid are reacted in a suitable volume of water and dioxane to maintain the internal temperature of the reaction between about 50° C. to about 80° C. In acetic acid alone, the reaction is too exothermic. Reaction temperature of over 100° C. are not preferred as decomposition may be observed. Preferrably, the reaction is maintained at 80° C. or below.

In certain embodiments, the compound of formula IV, the compound of formula V, water, dioxane, and acetic acid are stirred at about 50° C. to about 65° C. Other preferred temperatures are at about 58° C. to about 60° C.

In certain embodiments, the process comprises the step of adding zinc. Preferred temperature for these reactions include about 75° C. to about 85° C. Other temperatures are about 80° C. to about 85° C.; about 80° C. to about 82° C.

In preferred processes according to this invention, the zinc is added portionwise. The reaction is exothermic, therefore adding the zinc portion-wise helps maintain temperature and is also safer.

In certain embodiments of this invention (particularly in $R^3$) in alkylaryl and alkylheteroaryl groups, the aryl and heteroaryl is not alpha or beta relative to the position the alkyl is bound to the rest of the molecule. Preferably, the aryl and heteroaryl is at least at the gamma position or even farther from the bond. Aliphatic groups are preferably alkyl. Preferred forms of a $C_{1-12}$ group, is a $C_{1-6}$ group.

In other embodiments, $R^3$ is independently $C_{1-6}$ alkyl, preferably, each $R^3$ is independently $C_{1-3}$ alkyl. Most preferably, each $R^3$ is methyl.

In other embodiments, each $R^2$ and $R^3$ is independently methyl and $R^1$ is ethyl.

In other embodiments, $R^5$ is $C_{1-6}$ alkyl. Preferably, $R^5$ is methyl.

In other embodiments, The $R^3$ and $R^5$ is independently methyl.

In other embodiments, $R^2$, $R^3$, and $R^5$ is independently methyl and $R^1$ is ethyl.

Each of the general embodiments above (i.e., preparation of IV, IV-A, or IV-B, or and preparation of VII, VII-A, or VII-B) may be used separately or together in a process for preparing a compound of formula I, I-A, or I-B. Sample preparations of a compound of formula I, I-A, or I-B would be individual reactions such as those known to skilled practitioners, those of WO 03/087092, and/or those described herein in Examples 1–5.

Advantageously, the processes set forth in Examples 1–5 have been done and found to be applicable on a large scale to produce a compound of formula I, I-A, or I-B. Thus, one embodiment of this invention is as set forth in Example 1 or Example 3 alone or Example 1 and/or Example 3 in combination with any one or more of Example 2, Example 4, or Example 5.

Specific embodiments of this invention are those of the Examples herein.

Although the processes of this invention are depicted with a free amine, a free carboxylic acid, and an unsubstituted carbonyl group, each of these groups could be derivatized or protected as desired (see, e.g., T. W. Greene & P. G. M. Wuts, "Protective Groups in Organic Synthesis", $3^{rd}$ Ed., John Wiley & Sons, Inc., New York (1999).

Accordingly to a specific embodiment, this invention provides a process for preparing a compound:

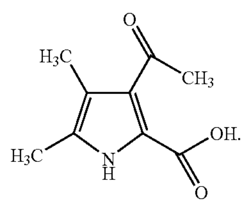

Although, the carboxylic acid prepared according to this invention may be used as a capping group, a skilled practitioner could envision other uses for the acid. Any such use that involves the processes provided herein, are part of this invention.

Depicted below in Scheme 1 is a specific embodiment of this invention, wherein each $R^2$, $R^3$, and $R^5$ is methyl and $R^1$ is ethyl. Each of the conversions I Scheme 1:

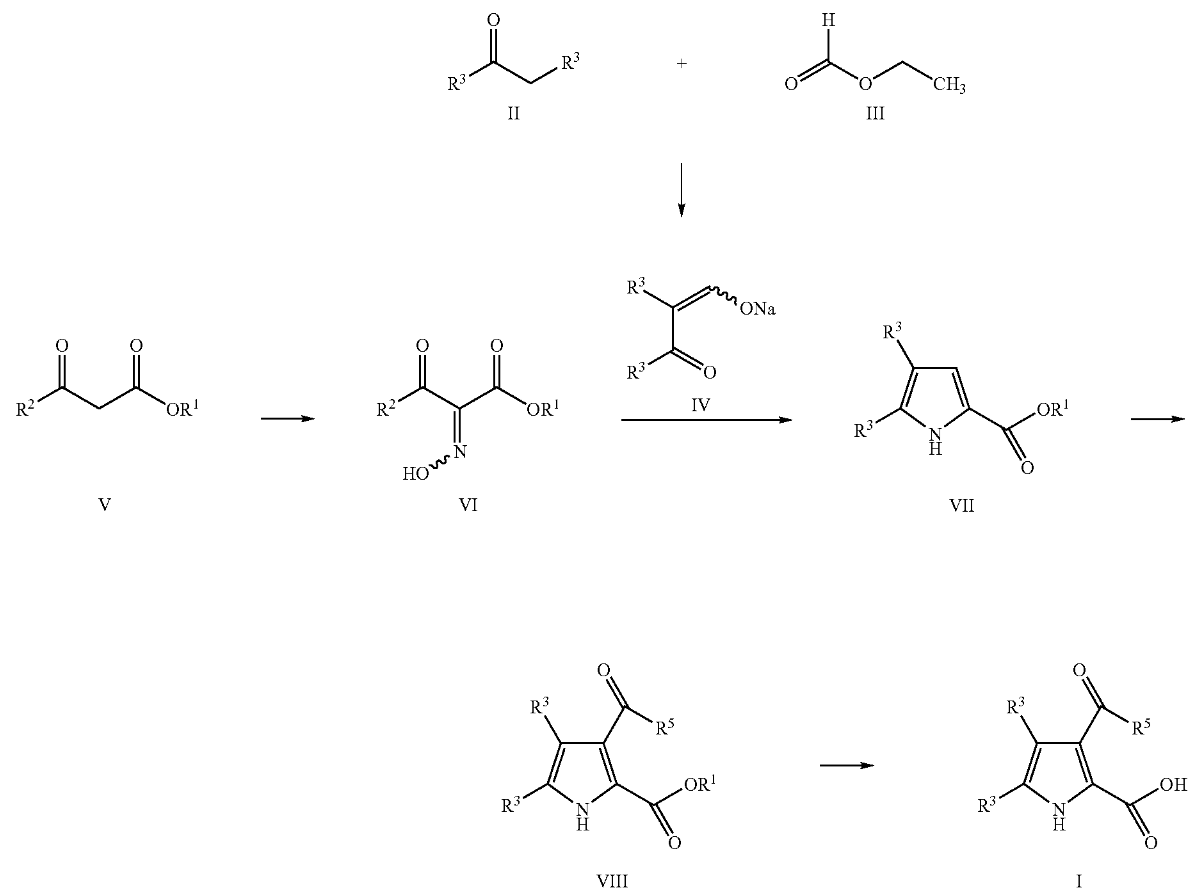

General Synthetic Methodology:

Process used in connection with this invention, unless otherewise stated, may be according to general methods known to those skilled in the art. Except for the embodiments set forth herein, other equivalent procedures to those of Scheme 1, as illustrated by the general procedures herein, and the preparative examples that follow may alternatively be used to synthesize various portions of the pyrrole carboxylic acid. General principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001; Greene & Wuts, Protective Groups in Organic Synthesis" John Wiley & Sons (1999) and the other editions of this book; the entire contents of each are hereby incorporated by reference.

In order that this invention be more fully understood, the following preparative and testing examples are set forth. These examples are for the purpose of illustration only and are not to be construed as limiting the scope of the invention in any way.

EXAMPLE 1

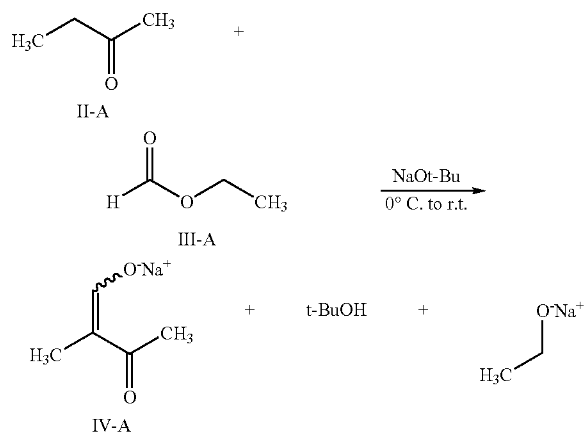

Materials

| Material | Mwt | Amount | Density | Moles | Eq. |
|---|---|---|---|---|---|
| Butanone, 99+% (II-A) | 72.11 | 1.0 kg | 0.805 | 13.87 | 1.0 |
| Ethyl formate, 97% (III-A) | 74.08 | 1.54 kg | 0.917 | 20.80 | 1.5 |
| Sodium t-butoxide 30 wt % in THF | 96.11 | 5.3 L | | 16.64 | 1.2 |
| Tetrahydrofuran | 72.11 | 1.6 L | 0.889 | | |

Method

Step 1: To a 12 L 3-neck round bottom flask, under nitrogen, equipped with a mechanical stirrer, thermometer, and an addition funnel, charge 1.0 kg of butanone.

Step 2: To the butanone charge 1.6 L of tetrahydrofuran.

Step 3: Cool the solution to 5° C.–10° C.

Step 4: To the cooled solution add 1.54 kg of ethyl formate.

Step 5: To the mixture add 5.3 L of 30 wt % sodium t-butoxide in tetrahydrofuran (Note 1).

Step 6: Stir the mixture overnight at 22°–26° C. (Note 2).

Step 7: Collect the precipitate by suction filtration.

Step 8: Rinse the filter cake with ~2.0 L of tetrahydrofuran.

Step 9: Pull vacuum on the filter cake for 1–2 hours.

Step 10: Dry the filter cake under high vacuum for 16–20 hours.

Results

Weight: 1.5 kg

Purity % (w/w) or % (AUC): See Note 3.

Molar yield or area yield: 80%

Process Efficiency

Maximum volume step—9.5 L

Minimum volume step—9.5 L

Notes

Note 1—The addition of 30 wt % sodium t-butoxide in tetrahydrofuran was carried out over 2 hours and the temperature was not allowed to increase above 20° C.

Note 2—There has not yet been developed an analytical method to monitor the reaction progress, but $^{1}H$ NMR, or infrared spectroscopy, could follow the consumption of butanone.

Note 3—The purity is usually confirmed by $^{1}H$ NMR and is ~90–95% the desired compound (the vinyl proton of the product at −9.0 ppm can be integrated against a singlet at ~8.4 ppm thought to be from the undesired regioisomeric ketoaldehyde sodium salt). The material also contains 4–5% water as determined by Karl Fisher analysis.

EXAMPLE 2

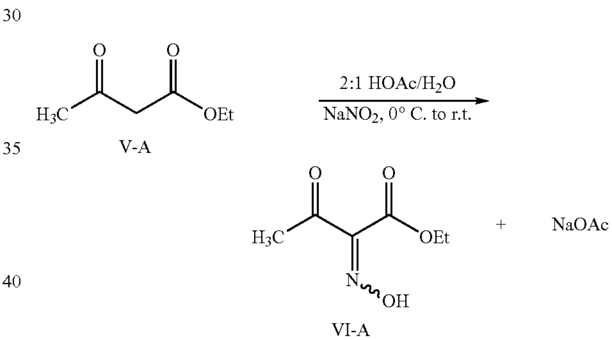

Materials

| Material | Mwt | Amount | Density | Moles | Eq. |
|---|---|---|---|---|---|
| Ethylacetoacetate, 99% (V-A) | 130.14 | 1.0 kg | 1.021 | 7.68 | 1.0 |
| Sodium nitrite, 97+% | 69.0 | 557 g | | 8.07 | 1.05 |
| Acetic acid, glacial, 100% | 60.05 | 2.0 L | 1.049 | | |
| Water | 18.0 | 4.0 L | | | |
| tert-Butyl methyl ether 99+% | 88.15 | 3.5 L | 0.740 | | |
| 10% Aqueous potassium carbonate | | 3.0 L | | | |
| Saturated sodium chloride | | 2.0 L | | | |

Process Detail

Step 1: Prepare 10% aqueous potassium carbonate solution: 300 g of potassium carbonate dissolved in 2.7 L of water.

Step 2: Prepare saturated sodium chloride solution: 529 g of sodium chloride dissolved in 1.4 L of water.

Step 3: Prepare aqueous sodium nitrite solution: 557 g of sodium nitrite dissolved in 1.0 L of water.

Step 4: Prepare ethylacetoacetate/glacial acetic acid solution: 1.0 kg of ethylacetoacetate dissolved in 2.0 L of glacial acetic acid.

Step 5: Charge to a 3.0 L 3-neck round bottom flask, equipped with a mechanical stirrer, thermometer, and an addition funnel, ethylacetoacetate/glacial acetic acid solution.

Step 6: Cool the solution to 3°–6° C.

Step 7: Charge the aqueous sodium nitrite solution to the ethylacetoacetate/glacial acetic acid solution (Note 1).

Step 8: Stir the reaction mixture at ambient temperature and monitor the reaction progress by $^1$H NMR (Note 2).

Step 9: Dilute the reaction mixture with 3.0 L of water.

Step 10: Extract the diluted reaction mixture with 3.5 L of tert-butyl methyl ether.

Step 11: Separate the layers.

Step 12: Extract the organic layer with 2.0 L of 10% aqueous potassium carbonate (Note 3).

Step 13: Separate the layers.

Step 14: Extract the organic layer with 1.0 L of 10% aqueous potassium carbonate.

Step 15: Separate the layers.

Step 16: Wash the organic layer with 2.0 L of saturated sodium chloride.

Step 17: Separate the layers.

Step 18: Concentrate the organic layer to a green colored oil.

Results

Weight: 1.2 kg

Purity % (w/w) or % (AUC): 95% AUC

Molar yield or area yield: 92%

Analytical

Method: HPLC: Zorbax SB Phenyl; 5 um, 4.6 mm i.d.×250 mm, 90% H2O/10% CH3CN/0.1% TFA to 10% water over 15 minutes, 10 μL injection, 1.0 mL/minute, run time=20 minutes, column temperature=50° C., λ=214 nm.

Retention Times

| Peak No. | Assignment | Retention Time | Rel Retention Time |
|---|---|---|---|
| 1 | Uncharacterized | 8.1 minutes | |
| 2 | VI-a | 8.4 minutes | |

Process Efficiency

Maximum volume step: 11 L

Minimum volume step: 4.5 L

Notes

Note 1: The sodium nitrite addition was carried out over 90 minutes, and the temperature was not allowed to increase above 25° C.

Note 2: A reaction time of 1–2 hours is typical, and the reaction is complete when the methylene protons of ethylacetoacetate are absent.

Sample preparation—2.0 mL reaction aliquot diluted with 2.0 mL of water and extracted with 3.0 mL of EtOAc. Separate layers, concentrate the organic layer, and dilute with $CDCl_3$.

Note 3: The base should be added cautiously to avoid excessive off-gassing.

EXAMPLE 3

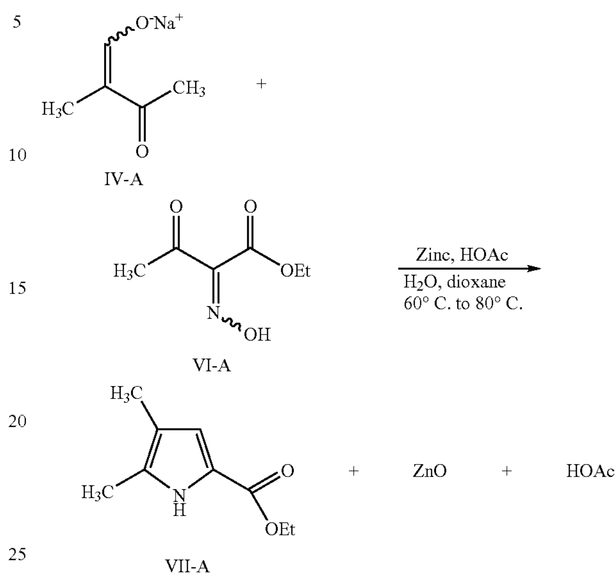

Materials

| Material | Mwt | Amount | Density | Moles | Eq |
|---|---|---|---|---|---|
| VI-A, 90% | 159.14 | 697 g | | 4.38 | 1.0 |
| IV-a, 95% | 122.10 | 619 g | | 4.81 | 1.1 |
| Zinc, 100% | 65.37 | 487 g | | 7.45 | 1.7 |
| Acetic acid, glacial, 100% | 60.05 | 763 g | 1.049 | 12.70 | 2.9 |
| Water | 18.0 | 7.4 L | | | |
| Dioxane | 88.11 | 1.4 L | 1.034 | | |
| tert-Butyl methyl ether | 88.15 | 5.0 L | 0.740 | | |

Process Detail

Step 1: Prepare aqueous IV-A solution: 619 g of IV-A dissolved in 1.5 L of water.

Step 2: To a 22 L 3-neck round bottom flask, under nitrogen, equipped with a mechanical stirrer, thermocouple/heating mantle apparatus, and an addition funnel, charge 697 g of VI-A.

Step 3: To the VI-A add 1.4 L of dioxane.

Step 4: To the solution add 3.4 L of water.

Step 5: To the solution add 763 g of acetic acid.

Step 6: To the mixture add aqueous IV-a solution.

Step 7: Heat the mixture to 580°–600° C.

Step 8: To the mixture add zinc (Note 1).

Step 9: Stir the mixture at 800°–82° C. and monitor the reaction completeness by HPLC (Notes 2 and 3).

Step 10: Cool the mixture to 25°–28° C.

Step 11: Extract the mixture with 5.0 L of tert-butyl methyl ether.

Step 12: Filter the bi-layered mixture through ordinary Whatman filter paper (Note 4).

Step 13: Separate the layers.

Step 14: Wash the organic layer with 2.5 L of water.

Step 15: Separate the layers.

Step 16: Dry the organic layer over 500 g of magnesium sulfate (Note 5).

Step 17: Remove the magnesium sulfate by filtration.

Step 18: Concentrate the filtrate to a dark brown solid.

Step 19: Dry the solid under vacuum at 40° C. for 16 hours.

Results

Weight: 512 g

Purity % (w/w) or % (AUC): 77% AUC (HPLC)

Molar yield or area yield: 54%

Analytical

In process control

HPLC: Zorbax SB Phenyl 4.6×250 mm i.d., 5 μm, 90% water/10% $CH_3CN$/0.1% TFA to 10% water over 15 minutes, flow rate=1.0 mL/minute, 10 μL injection, column temperature=50° C., λ=214 nm.

Sample preparation: 3 drops of reaction mixture dissolved in 1.0 mL of 1:1 water/$CH_3CN$.

Retention Times

| Peak No. | Assignment | Retention Time | Rel Retention Time |
|---|---|---|---|
| 1 | VI-A | 8.5 minutes | |
| 2 | VII-A | 11.4 minutes | |
| 3 | Multiple smaller uncharacterized peaks. | | |

Process Efficiency

Maximum volume step—14 L (Step 11).

Minimum volume step—9.0 L (Step 6).

Notes

Note 1: The zinc is added in 10–15% portions over 90 minutes. The addition of each portion is accompanied by a temperature increase of 70°–100° C. Before the next addition, the temperature is adjusted to 70° C. with a cool water bath.

Note 2: The mixture may or may not reflux at this temperature, but the reflux temperature is probably 82°–85° C.

Note 3: The reaction is generally complete after this 30 minute stir period.

Note 4: The filtration time is dependent on the amount of inorganic precipitates and in some cases has required 60 minutes.

Note 5: On scale, the drying agent could probably be replaced by a solvent exchange into dichloroethane (the solvent for the next reaction).

EXAMPLE 4

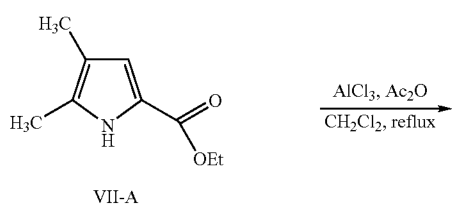

-continued

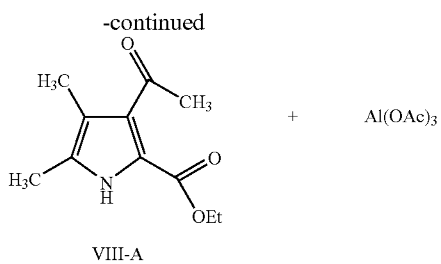

Materials

| Material | Mwt | Amount | Density | Moles | Eq. |
|---|---|---|---|---|---|
| 1. VII-A (80%) | 167.22 | 223 g | | 1.33 | 1.0 |
| 2. Aluminum chloride | 133.34 | 1.0 kg | | 8.0 | 6.0 |
| 3. Acetic anhydride | 102.07 | 408 g | 1.082 g/mL | 4.0 | 3.0 |
| 4. Dichloromethane | 84.93 | 3.0 L | | | |
| 5. Saturated sodium chloride | | 800 mL | | | |

Process Detail

Step 1: Prepare saturated sodium chloride solution: 220 g of sodium chloride dissolved in 580 mL of water.

Step 2: Prepare acetic anhydride/dichloromethane solution: 408 g of acetic anhydride dissolved in 220 mL of dichloromethane.

Step 3: Prepare VII-A/dichloromethane solution: 223 g of VII-A dissolved in 1.1 L of dichloromethane.

Step 4: Charge 1.0 kg of aluminum chloride to a 12 L 3-neck round bottom flask that is under a nitrogen atmosphere, and is equipped with a water cooled condenser, addition funnel, and thermocouple.

Step 5: Add 880 mL of dicloromethane to the aluminum chloride.

Step 6: Cool the aluminum chloride/dichloromethane suspension to 5° 10° C. with an ice water bath.

Step 7: Add acetic anhydride/dichloromethane solution to the aluminum chloride suspension (Note 1).

Step 8: Stir the aluminum chloride/acetic anhydride complex for 30 minutes (Note 2).

Step 9: Add VII-A/dichloromethane solution to aluminum chloride/acetic anhydride complex (Notes 3 and 4).

Step 10: Fit the 12 L round bottom flask with a heating mantle.

Step 11: Heat the reaction mixture at reflux (34°–37° C) and monitor the consumption of VII-A by HPLC (Notes 5 and 6).

Step 12: Cool the reaction mixture to 24°–26° C. with a cool water bath.

Step 13: Transfer the black mixture to a 10 L carboy.

Step 14: Charge 4.4 L of water to the 12 L vessel.

Step 15: Cool the water to 50°–100° C. with an ice water bath.

Step 16: Quench the VIII-A mixture into the water (Note 7).

Step 17: Separate the layers (Note 8).

Step 18: Wash the aqueous layer with 800 mL of dichloromethane.

Step 19: Separate the layers.

Step 20: Combine the organic layers.

Step 21: Wash the combined organic layers with 800 mL of saturated sodium chloride.

Step 22: Separate the layers.

Step 23: Using rotary evaporation at reduced pressure, concentrate the organic layer to a black solid.

Results

Weight: 223 g

Purity % (w/w) or % (AUC): 80% AUC

Molar yield or area yield: 64% corrected yield.

Analytical

Method (HPLC)— Zorbax SB Phenyl; 5 um, 4.6 mm i.d.×250 mm length; 90% water/10% acetonitrile/0.1% trifluoroacetic acid to 90% acetonitrile over 15 minutes, run time=20 minutes, injection volume=10 μL, flow rate=1.0 mL/minute, column temperature=50° C., wavelength=214 nm.

Retention Times

| Peak No. | Assignment | Retention Time |
|---|---|---|
| 1 | VII-A | 11.4 minutes |
| 2 | VIII-A | 10.6 minutes |

Process Efficiency

Maximum volume step—8.2 L

Minimum volume step—1.9 L

Notes

Note 1: The addition was carried out dropwise over 25–30 minutes and the temperature was not allowed to increase above 27° C.

Note 2: The mixture should be homogeneous and light green colored.

Note 3: The addition was carried out dropwise over 25–30 minutes and the temperature was not allowed to increase above 30° C.

Note 4: The mixture will be homogeneous and black colored.

Note 5: A reaction time of 1–2 hours is typical.

Note 6: Sample preparation: 3 drops of reaction mixture dissolved in 1.0 mL of 50% aqueous acetonitrile. Method (HPLC): see under Analytical section.

Note 7: The quench was carried out dropwise over ~2 hours and the temperature was not allowed to increase above 27° C.

Note 8: The bi-layered mixture will be black and the interface might not be clear. If the interface is not clear, then removal of the organic layer by weight or volume is necessary.

EXAMPLE 5

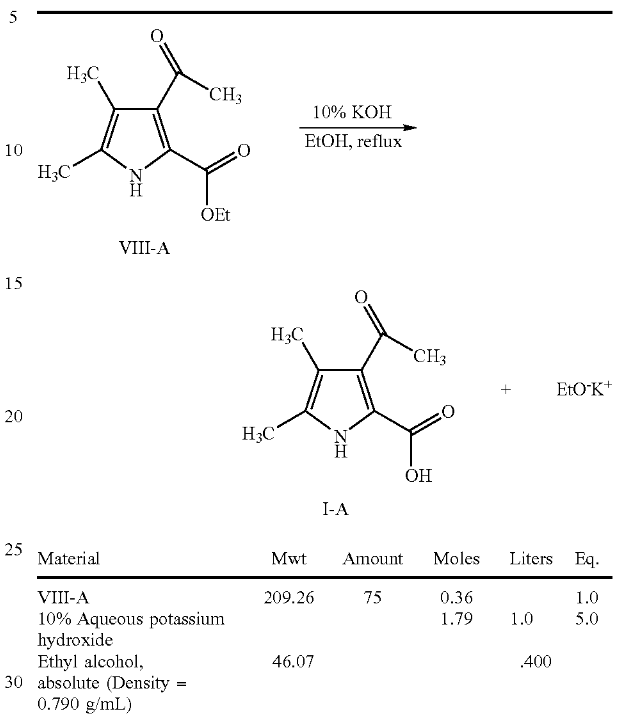

| Material | Mwt | Amount | Moles | Liters | Eq. |
|---|---|---|---|---|---|
| VIII-A | 209.26 | 75 | 0.36 | | 1.0 |
| 10% Aqueous potassium hydroxide | | | 1.79 | 1.0 | 5.0 |
| Ethyl alcohol, absolute (Density = 0.790 g/mL) | 46.07 | | | .400 | |

Procedure:

Step 1: Prepare 10% aqueous potassium hydroxide solution: 100 g of potassium hydroxide pellets dissolved in 900 mL of water (Note 1).

Step 2: Prepare 2 N hydrochloric acid solution: 150 mL of concentrated hydrochloric acid dissolved in 750 mL of water (Note 2).

Step 3: To a 2.0 L 3-neck round bottom flask charge 75 g of VIII-A.

Step 4: To the VIII-A add 1.0 L of 10% aqueous potassium hydroxide.

Step 5: To the heterogeneous solution add 75 mL of ethyl alcohol.

Step 6: Heat the mixture at 650°–70° C., and monitor the reaction progress by HPLC (Notes 3 and 4).

Step 7: Cool the mixture to 20°–25° C.

Step 8: To the mixture add 900 mL of 2 N hydrochloric acid (Note 5).

Step 9: Cool the precipitated mixture to 150°–20° C. and hold at that temperature for 30 minutes.

Step 10: Collect the precipitate by suction filtration and pull the filter cake dry for 1 hour.

Step 11: Take the filter cake up in 325 mL of ethyl alcohol.

Step 12: Heat the heterogeneous mixture at 550°–60° C. for 30–35 minutes.

Step 13: Allow the mixture to cool to 20°–25° C. and then hold at 5°–10° C. overnight (Note 6).

Step 14: Collect the brown precipitate by suction filtration.

Step 15: Dry the I-a under high vacuum at ambient temperature until a constant weight (Note 7).

Notes:

Note 1: The dissolution of potassium hydroxide is exothermic and the solution should be prepared with cooling.

Note 2: The dissolution of concentrated hydrochloric acid in water is exothermic and the solution should be prepared with cooling.

Note 3: A reaction time of 30–60 minutes is typical, and the reaction is complete when the starting material is consumed.

Note 4: HPLC method: Zorbax SB Phenyl, 5 um, 4.6 mm i.d.×250 mm length; 90% $H_2O$/10% $CH_3CN$/0.1% TFA to 10% $H_2O$/90% $CH_3CN$/0.1% TFA over 15 minutes, run time=20 minutes, 10 uL injection, 1.0 mL/minute flow rate, column temperature=50° C., λ=214 nm.

Retention time of VIII-a=10.9 minutes

Retention time of I-a=9.7 minutes

Less intense uncharacterized impurities will also be detected.

Sample Preparation: 2 drops of reaction mixture in ~1.0 mL of $CH_3CN$/2–3 drops of water.

Note 5: The addition of 2 N hydrochloric acid was carried out over 20–25 minutes. The temperature was not allowed to increase above 30° C. The solution pH ~2.0–4.0 to universal pH paper. Over acidification might cause gumming and a less quantitative recovery of crude product.

Note 6: Holding at 5°–10° C. might not be necessary, but that remains to be determined.

Note 7: The I-a is analyzed by HPLC (see method in Note 4), and has assayed (percent area ratio) at 98%–100% pure.

All of the documents cited herein, are incorporated herein by reference.

All documents cited herein are incorporated by reference. Also incorporated by reference is U.S. provisional application 60/515,283.

Any embodiments (including preferred embodiments disclosed for embodiment A or B, apply to the other embodiment.

While we have described a number of embodiments of this invention, it is apparent that our basic examples may be altered to provide other embodiments that utilize the processes of this invention. Therefore, it will be appreciated that the scope of this invention is to be defined by any claims rather than by the specific embodiments that have been represented by way of example above.

What is claimed is:

1. A process for preparing a compound of formula I-a:

I-a comprising:

a) combining an aqueous solution of the compound of formula IV-a:

IV-a wherein $R^3$ is $C_{1-12}$ aliphatic, $C_{3-12}$ alkyl-cycloaliphatic, $C_{3-12}$ alkyl-aryl, $C_{3-12}$ alkyl-heteroaryl, or $C_{3-12}$ alkyl-cycloaliphatic;

$R^5$ is $C_{1-12}$ aliphatic, aryl, heteroaryl, $C_{1-12}$ alkyl-cycloaliphatic, $C_{1-12}$ aliphatic-aryl, $C_{1-12}$ aliphatic-heteroaryl or $C_{1-12}$ aliphatic-cycloaliphatic;

with a compound of formula V-a

V-a wherein $R^1$ and $R^2$ are each independently $C_{1-6}$aliphatic; in the presence of zinc, dioxane, water, and optionally an additional suitable solvent to form a compound of formula VI

VI b) acylating the compound of formula VI with a suitable acylating agent to form the compound of formula IX

IX and c) hydrolyzing the compound of formula IX under suitable hydrolysis conditions to form the compound of formula I-a.

2. The process according to claim 1 wherein the compound of formula VI is reacted with $R^5$-X or $R^5C(=O)$—O—$C(=O)R^5$ to form the compound of formula IX wherein X is a suitable leaving group;

$R^5$ is $C_{1-12}$ aliphatic, aryl, heteroaryl, $C_{1-12}$ aliphatic-cycloaliphatic, $C_{1-12}$ aliphatic-aryl, $C_{1-12}$ aliphatic-heteroaryl, or $C_{1-12}$ aliphatic-cycloaliphatic.

3. The process according to claim 2, wherein the acylation conditions comprise: heating the compound with $AllC_3$ and $R^5C(=O)—O—C(=O)R^5$ to form the compound of formula IX.

4. The process according to claim 3, wherein the acylation conditions comprise: heating the compound with $AlCl_3$ and $Ac_2O$ in refluxing dichloromethane to form the compound of formula IX wherein $R^5$ is methyl.

5. The process according to claim 1 wherein the hydrolysis conditions comprise: a suitable base, a suitable solvent, and a reaction temperature between 20–100° C.

6. The process according to claim 5 wherein the base is $M(OH)_n$, wherein M is a metal selected from lithium, sodium, potassium, cesium, magnesium, and calcium and n is 1–2.

7. The process according to claim 6 wherein the solvent is an alcoholic solvent.

8. The process according to claim 7 wherein the base is KOH, the solvent is EtOH, and the temperature is that of refluxing ethanol.

9. The process according to any one of claims 1, 2–4 or 5–8 wherein the compound of formula IV, the compound of formula V, and a suitable acid are reacted in water and a suitable volume of an organic solvent to keep the reaction mixture in solution.

10. The process according to any one of claims 1, 2–4 or 5–8 wherein the compound of formula IV, the compound of formula V, and acetic acid are reacted in a suitable volume of water and dioxane to maintain the internal temperature of the reaction between about 50° C. to about 80° C.

11. The process according to any one of claims 1, 2–4 or 5–8 wherein the compound of formula IV, the compound of formula V, water, dioxane, and acetic acid are stirred at about 50° C. to about 65° C.

12. The process according to claim 11 wherein the reaction mixture is stirred at about 58° C. to about 60° C.

13. The process according to any one of claims 1, 2–4 or 5–8 further comprising the step of adding zinc.

14. The process according to claim 13 further comprising stirring the mixture at about 75° C. to about 85° C.

15. The process according to claim 14 wherein the mixture is stirred at about 80° C. to about 85° C.

16. The process according to claims 1, 2–4 or 5–8 wherein the mixture is stirred at about 80° C. to about 82° C.

17. The process according to any one of claims 1, 2–4 or 5–8 wherein the zinc is added portionwise.

18. The process according to any one of claims 1, 2–4 or 5–8 wherein each $R^3$ is independently $C_{1-6}$alkyl.

19. The process according to claim 18 wherein each $R^3$ is independently $C_{1-3}$alkyl.

20. The process according to claim 19 wherein each $R^3$ is independently methyl.

21. The process according to any one of claims 1, 2–4 or 5–8 wherein each $R^2$ and $R^3$ is independently methyl and $R^1$ is ethyl.

22. The process according to any one of claims 1, 2–4 or 5–8 wherein $R^5$ is $C_{1-6}$alkyl.

23. The process according to any one of claims 1, 2–4 or 5–8 wherein $R^5$ is methyl.

24. The process according to any one of claims 1, 2–4 or 5–8 wherein each $R^3$ and $R^5$ is independently methyl.

25. The process according to claim 24 wherein each $R^2$, $R^3$, and $R^5$ is independently methyl and $R^1$ is ethyl.

* * * * *